(12) United States Patent
Chandler et al.

(10) Patent No.: US 7,747,328 B2
(45) Date of Patent: Jun. 29, 2010

(54) METHOD AND APPARATUS FOR TREATING A WOUND

(75) Inventors: Mark Chandler, Southern Pines, NC (US); Richard Nagle, London (GB)

(73) Assignee: Wound Solutions Limited, London (GB)

( * ) Notice: Subject to any disclaimer, the term of this patent is extended or adjusted under 35 U.S.C. 154(b) by 1094 days.

(21) Appl. No.: 11/019,237

(22) Filed: Dec. 23, 2004

(65) Prior Publication Data

US 2006/0142817 A1 Jun. 29, 2006

(51) Int. Cl.
*A61N 1/18* (2006.01)
(52) U.S. Cl. .......................................... 607/50; 601/15
(58) Field of Classification Search .................. 607/50, 607/66, 67, 3, 144, 149; 601/15, 21
See application file for complete search history.

(56) References Cited

U.S. PATENT DOCUMENTS

| | | | |
|---|---|---|---|
| 4,117,846 A | 10/1978 | Williams | |
| 4,556,051 A | 12/1985 | Maurer | |
| 4,738,250 A | 4/1988 | Fulkerson et al. | |
| 4,846,181 A | 7/1989 | Miller | |
| 4,895,154 A | 1/1990 | Bartelt et al. | |
| 4,982,742 A * | 1/1991 | Claude ........................ | 607/50 |
| 5,158,081 A * | 10/1992 | McWhorter et al. ........... | 607/50 |
| 5,395,398 A | 3/1995 | Rogozinski | |
| 5,450,845 A | 9/1995 | Axelgaard | |
| 5,643,332 A | 7/1997 | Stein | |
| 5,690,692 A | 11/1997 | Fleming | |

(Continued)

FOREIGN PATENT DOCUMENTS

EP  0367 320  5/1990

(Continued)

OTHER PUBLICATIONS

R.J. Abboud et al., "Lower limb muscle dysfunction may contribute to foot ulceration in diabetic patients", Clinical Biomechanics, vol. 15, Issue 1, Jan. 2000, pp. 37-45.

(Continued)

*Primary Examiner*—Carl H Layno
*Assistant Examiner*—Brian T Gedeon
(74) *Attorney, Agent, or Firm*—Dickstein Shapiro LLP

(57) ABSTRACT

A method of treating a wound comprising the steps of placing a pair of electrodes placed spaced apart in the region of a wound and applying a predetermined sequence of current waveforms across the electrodes. The sequence of current waveforms comprises a first waveform comprising a series of current pulses having an amplitude in a range of from 80 to 300 µA, having a frequency in a range from 0.5 to 1.5 pulses per second and a pulse width in a range from 333 to 1000 ms, a second waveform comprising a series of current pulses having an amplitude in a range of from 20 to 60 µA, having a frequency in a range from 2 to 4 pulses per second and a pulse width in a range from 125 to 250 ms and a third waveform comprising a series of current pulses having an amplitude in a range of from 250 to 640 µA, having a frequency in a range of from 80 to 120 pulses per second and a pulse width in a range from 4 to 6 ms.

36 Claims, 8 Drawing Sheets

U.S. PATENT DOCUMENTS

| | | |
|---|---|---|
| 5,974,342 A | 10/1999 | Petrofsky |
| 6,002,965 A | 12/1999 | Katz et al. |
| 6,282,448 B1 | 8/2001 | Katz et al. |
| 6,363,284 B1 | 3/2002 | Nachum |
| 6,393,326 B1 | 5/2002 | Nachum |
| 6,941,173 B2 | 9/2005 | Nachum |
| 2004/0030270 A1* | 2/2004 | Johnson ................ 601/15 |
| 2004/0054384 A1 | 3/2004 | Nachum |
| 2004/0147977 A1 | 7/2004 | Petrofsky |
| 2005/0119715 A1 | 6/2005 | Petrofsky |

FOREIGN PATENT DOCUMENTS

| | | |
|---|---|---|
| GB | 2 404 858 A | 2/2005 |
| GB | 2 406 519 A | 4/2005 |
| WO | WO 90/09810 | 9/1990 |
| WO | WO 97/15348 | 5/1997 |
| WO | WO 98/40121 | 9/1998 |
| WO | WO 98/52642 | 11/1998 |
| WO | WO 99/04852 | 2/1999 |
| WO | WO 99/64105 | 12/1999 |
| WO | WO 01/03768 A1 | 1/2001 |
| WO | WO 01/91697 A2 | 12/2001 |
| WO | WO 02/20085 A2 | 3/2002 |
| WO | WO 02/056960 A2 | 7/2002 |
| WO | WO 03/082400 A2 | 10/2003 |
| WO | WO 2004/045484 A2 | 6/2004 |

OTHER PUBLICATIONS

P.E. Houghton et al., "Effect of Electrical Stimulation on Chronic Leg Ulcer Size and Appearance", Physical Therapy, vol. 83, No. 1, Jan. 2003.

L.A. Lavery et al., "Reducing Dynamic Foot Pressure in High-Risk Diabetic Subjects With Foot Ulcerations. A Comparison of Treatments", Diabetes Care, vol. 19, Issue 8, American Diabetes Assoc. ,1996.

J.J. Wertsch et al., "Plantar Pressures With Total Contact Casting", Journal of Rehabilitation Research and Development, vol. 32, No. 3, Oct. 1995, pp. 205-209.

"Lifewave", http://proceedings.jbjs.org.uk/cgi/content/abstract/88-B/SUPP_II/333-c .

* cited by examiner

METHOD AND APPARATUS FOR TREATING A WOUND

FIELD OF THE INVENTION

The present invention generally relates to a method and apparatus for treating a wound. In particular, the invention relates to a method and apparatus for treating a wound involving application of electrical signals to the region of the wound.

BACKGROUND OF THE INVENTION

Chronic wounds such as venous ulcers which do not heal, represent a serious problem to sufferers and healthcare providers. The prevalence of active venous ulcers in the adult population is high and their treatment is very costly to healthcare services. A venous ulcer is an area of damage to the skin that fails to heal after several weeks. They occur when the veins and muscles in the lower legs are weak and cannot efficiently pump the blood back to the heart as a result of damaged valves. Gravity then causes the blood to pool in the lower legs. The pooling blood eventually leaks out of the veins and into the surrounding tissue causing the tissue to swell which then leads to wounds and ulcers. Such wounds may be extremely painful and grow to a considerable size. Applying increased external pressure to the legs with compression bandaging or graduated compression hosiery, for example, has been used to assist in the healing of venous leg ulcers and gravitational eczema. The increased pressure forces the blood back into the veins creating an improved blood flow thereby allowing the ulcers to heal. Compression bandages or graduated compression hosiery apply pressure to the leg, with greater pressure near the ankle and reduced pressure higher up. This forces the blood to keep circulating away from the lower leg.

Studies have shown that the process of healing, growth and regeneration in living tissue is brought about by the flow of endogenous electrical current. It has been suggested that the application of external microcurrents to injured tissue can assist the body's natural healing process by augmenting the flow of current through the injured tissue. The application of electrical signals to injured tissue as a form of therapy is known as electrotherapy and has been described in various publications.

U.S. Pat. No. 4,982,742 describes a method and apparatus for facilitating the healing of soft tissue wounds involving the application of a single bi-phase microcurrent waveform to a selected area of tissue. The waveform is characterised by a frequency ranging from 10 to 50 Hz and an amplitude ranging between 100 and 1000 µA. The waveform is delivered by a disposable bandage containing an integrated circuit and power source.

Similarly the method described in U.S. Pat. No. 6,393,326 uses one waveform throughout treatment. The electrical treatment signal disclosed in this document is characterised by a bipolar voltage waveform at a frequency of between 2 Hz and 10 Hz. This method is particularly adapted to the treatment of bedsores which are known to have substantially zero electrical activity.

EP367320 also relates to a system for the treatment of wounds by electric stimulation.

The document discloses a waveform generator adapted to generate either a direct current signal or a pulsed signal comprising pulses with a pulse width of less than 1 ms. It further discloses that optimal pulse width is about 0.1 ms. The DC current application is believed to produce wound healing and the pulse signals when applied directly into the wounds are said to produce a pain-relief effect.

None of the above methods is specifically adapted to the treatment of venous ulcers. In addition, all of the above described methods are applied on their own and are not used simultaneously with other methods of wound healing There is therefore a recognised need for an effective method for promoting the healing of chronic wounds such as venous ulcers. It would be particularly advantageous to have a method of electrotherapy tailored to the healing of venous ulcers.

SUMMARY OF THE INVENTION

The present invention provides a method of and an apparatus for treating a wound.

In one aspect of the invention the method includes placing a plurality of electrodes spaced apart in the region of a wound, placing a covering exerting pressure on the region of the wound to improve blood flow in the region of the wound, and applying a sequence of predetermined waveforms across a pair of electrodes placed spaced apart in the region of the wound. The sequence of waveforms includes a first waveform comprising a series of current pulses having an amplitude of between 80 and 300 µA, having a frequency of between 0.5 and 1.5 pulses per second and a pulse width of between 333 and 1000 ms, a second waveform comprising a series of current pulses having an amplitude of between 20 and 60 µA, a frequency of between 2 and 4 pulses per second and a pulse width of between 125 and 250 ms, and a third waveform comprising a series of current pulses having an amplitude of between 250 and 640 µA, having a frequency of between 80 and 120 pulses per second and a pulse width of between 4 and 6 ms. The application of waveforms with these ranges of parameters increases efficacy in the healing of wounds. Thus in accordance with this aspect of the invention, the benefit of conventional pressure bandages and an electrotherapy treatment specific for the treatment of wounds caused by blood pooling such as venous ulcers is achieved.

In one embodiment, the polarity of the electrodes is reversed approximately every 5 to 15 seconds during application of the first waveform. In another embodiment, the polarity of the electrodes is reversed approximately every 5 to 15 seconds during application of the second waveform. In a further embodiment, the polarity of the electrodes is reversed approximately every 5 to 15 seconds during application of the third waveform. In an even further embodiment, the polarity of the electrodes is reversed approximately every 5 to 15 seconds during application of all the waveforms.

In one embodiment, the first waveform comprises a series of current pulses having an amplitude of substantially 100 µA, a frequency of substantially 1 pulse per second and a pulse width of substantially 500 ms, the second waveform comprises a series of current pulses having a amplitude of substantially 40 µA, a frequency of substantially 3 pulses per second and a pulse width of substantially 166 ms, the third waveform comprises a series of current pulses having an amplitude of substantially 320 µA, a frequency of substantially 100 pulses per second and a pulse width of substantially 5 ms.

In an embodiment, the electrodes are positioned in contact with skin around the wound.

In an embodiment, each electrode of a pair of electrodes is positioned on opposite sides of the wound to one another so that the current passes under the wound.

In an embodiment, each electrode is placed approximately 1 cm from an edge of the wound.

In an embodiment, each waveform is generated over a period of time ranging from 5 to 30 minutes.

In an embodiment, the first waveform is generated over a period of time ranging from 5 to 10 minutes, the second waveform is generated over a period of time ranging from 10 to 20 minutes and the third waveform is generated over a period of time ranging from 15 to 30 minutes.

In one embodiment, the pulses are substantially rectangular. This encompasses pulses which are functionally rectangular or square.

In one embodiment, the sequence of waveforms is repeated thus providing treatment over a longer period of time if required.

In another aspect of the invention a method of treating a wound involves placing a plurality of electrodes in contact with skin in a region peripheral to the wound, placing a compression covering over the electrodes and the region of the wound to reduce pooling of blood in the region of the wound and applying an electrical current to the plurality of electrodes. This aspect of the present invention provides simultaneous conventional pressure bandage treatment and electrotherapy treatment to provide an improved method of treating wounds.

In one embodiment, the end of each electrode extends beyond the outermost edges of the wound so that the entire surface of the wound is positioned between two electrodes.

In one embodiment, each end of each electrode extends beyond the outermost edges of the wound by approximately 1.0 to 1.5 cm.

In a further aspect of the invention, the method of treating a wound includes placing a plurality of electrodes in contact with skin in a region peripheral to the wound and applying a sequence of specific current waveforms between the electrodes. The sequence of specific waveforms includes a first waveform comprising a series of current pulses having an amplitude in a range of from 80 to 300 µA, having a frequency in a range from 0.5 to 1.5 pulses per second and a pulse width in a range from 333 to 1000 ms, a second waveform comprising a series of current pulses having an amplitude in a range of from 20 to 60 µA, having a frequency in a range from 2 to 4 pulses per second and a pulse width in a range from 125 to 250 ms and a third waveform comprising a series of current pulses having an amplitude in a range of from 250 to 640 µA, having a frequency in a range of from 80 to 120 pulses per second and a pulse width in a range from 4 to 6 ms. The application of this sequence of waveforms optimises wound healing. This aspect of the invention provides a new and improved electrotherapy treatment wherein the electrodes are not placed on the wound but in the periwound, thus avoiding deteriously interfering with the wound healing process and allowing for the administering of electrical current therapy through the regenerative tissue under the wound.

The apparatus according to the invention includes a waveform generator adapted to generate a predetermined sequence of waveforms comprising three waveforms and output connectors for connection to one or more pair of electrodes for applying the sequence of waveforms under the wound.

In one embodiment, the apparatus includes a polarity switch for reversing the polarity of the electrodes.

In an embodiment, the waveform generator is pre-programmed with one or more programs for generating one of said waveforms or a pre-determined sequence of said waveforms.

In one embodiment, the apparatus includes a user interface for selecting one of said waveforms or a predetermined sequence of said waveforms.

In one embodiment, the apparatus includes a second waveform generator for supplying a predetermined sequence of waveforms to a second pair of electrodes.

The method of treating a wound according to the invention has the advantage that it is capable of working in combination with other methods promoting the healing of venous ulcers such as the application of compression bandaging to the area of treatment. In addition, it is beneficial to have a method of treatment consisting of different treatment phases. It is also advantageous to have a method for promoting the healing of wounds that is non-invasive, that is easy to apply and that is capable of being used on a long term basis.

BRIEF DESCRIPTION OF THE DRAWINGS

Embodiments of the invention will now be described with reference to the accompanying drawings, in which.

DESCRIPTION OF THE EMBODIMENTS

Figure 1:
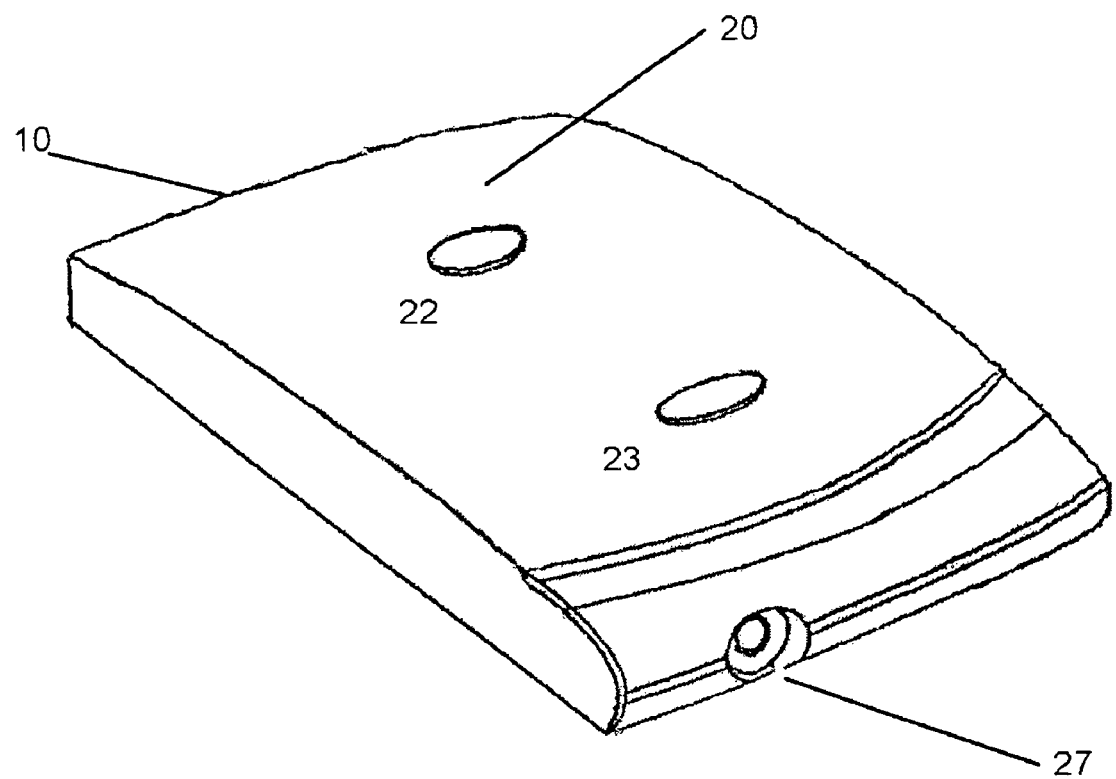
FIG. 1 is a perspective view of a device for generating electrical signals according to an embodiment of the present invention.

FIG. 1 is a perspective view of a device 10 for applying electrical signals to an area of tissue according to an embodiment of the present invention. The electrotherapy device 10 comprises a housing 20, an electrode port 27, an input switch 23 and an on/off switch 22. The input switch 23 and the on/off switch 22 may be the push button type. The housing 20 encloses a channel 30.

Figure 2:
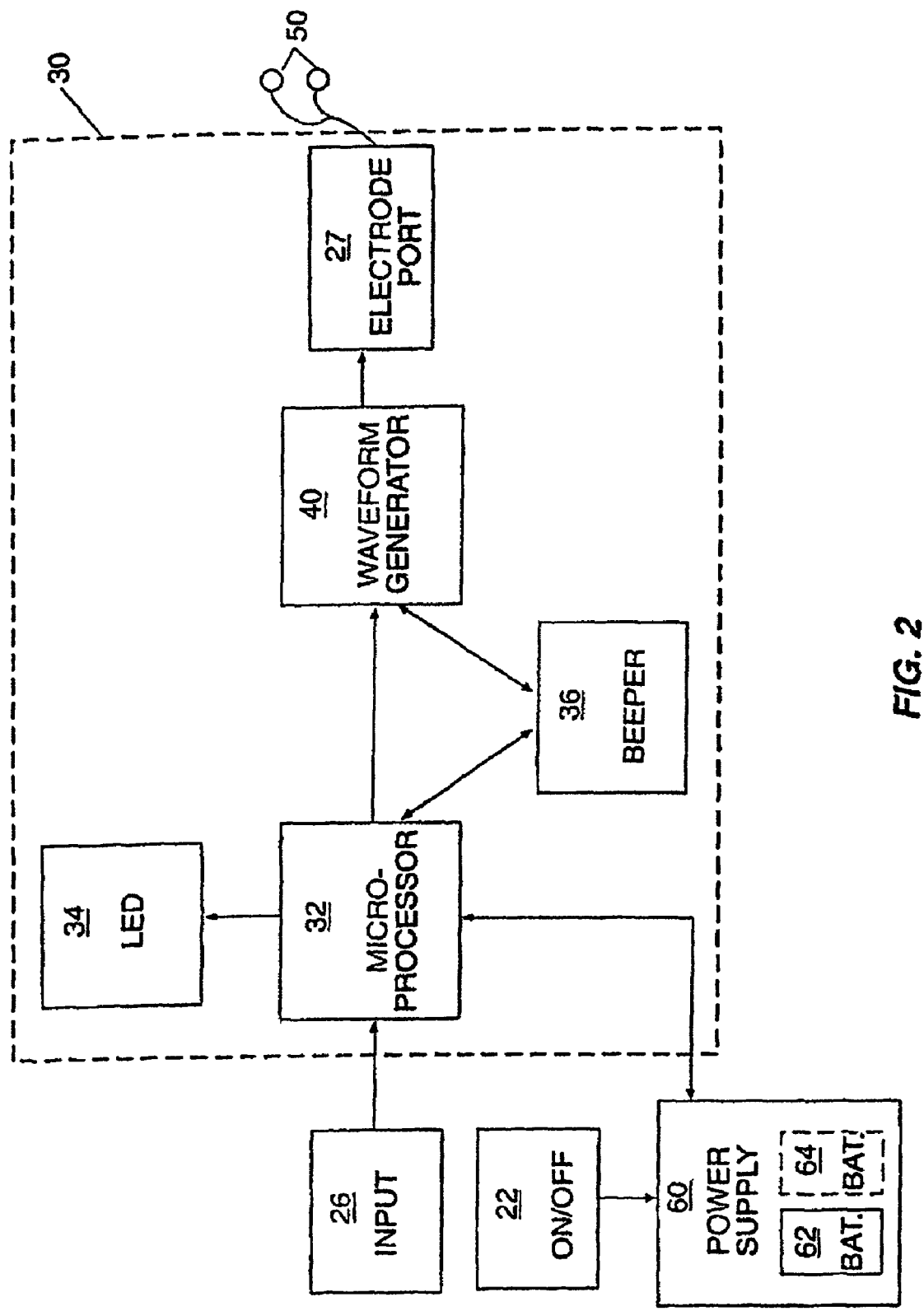
FIG. 2 is a schematic diagram showing one channel of a device for generating electrical signals according to the embodiment of the present invention.

FIG. 2 is a schematic diagram of the device 10 showing the channel 30. The channel 30 includes an electrode port 27, a microprocessor 32, a waveform generator 40, LEDs 34 and a beeper 36. The channel 30 is connected to the on/off switch 22, input switch 23, a power supply 60 and a pair of electrodes 50. The electrodes 50 may be of any type known in the art of electrotherapy. The power supply 60 supplies the microprocessor and the rest of the channel 30 with power. The power supply includes a battery which supplies power to the channel 30. Turning on the device 10 via the on/off switch 22 activates the power supply 60, which in turn controls the on/off stage of the battery 62. In this embodiment the power supply converts the battery voltage to a supply logic level of five volts.

The microprocessor 32 controls and/or monitors voltage, input switch 23, status LEDs 34, beeper 36 and the waveform generator 40. The waveform generator 40 receives signals from the microprocessor 32, transforms them into the appropriate current waveforms, and supplies the waveforms to the electrode port 27. The electrodes 50 transfer the waveforms from the electrode port 27 to the tissue to be treated. Input switch 23 and on/off switch 22 are resistor multiplexed into an analog port of the microprocessor 32.

The status of the device 10 is indicated by LEDs 34, controlled by microprocessor 32. Beeper 36 is activated when the device 10 detects high resistance between the individual electrodes of the electrode pair 50, indicating that the electrodes 50 are not making proper contact with the portion of the body to be treated. Such a situation is called a pad open condition. Beeper 36 is also activated when a low battery voltage is detected.

The device 10 is activated via on/off switch 22. Once energized, the microprocessor checks switch 23. Switch 23 is used to start a pre-programmed three stage waveform treatment program. The microprocessor 32 sends appropriate signals to the waveform generator 40 based on the pre-programmed three stage waveform treatment program to cause the appropriate signals to be sent to the electrodes 50. The microprocessor also instructs the LEDs and the beeper 36 to indicate the appropriate status. The device automatically cycles through the three stage treatment program when switch 23 is pressed, and automatically switches off when the cycle of treatment stages has finished. During the treatment program a ticking noise is emitted by the device 10 to indicate that the program is running. The beeper 36 emits a series of beeps at the end of the treatment program to indicate that the program has finished.

Figure 3:
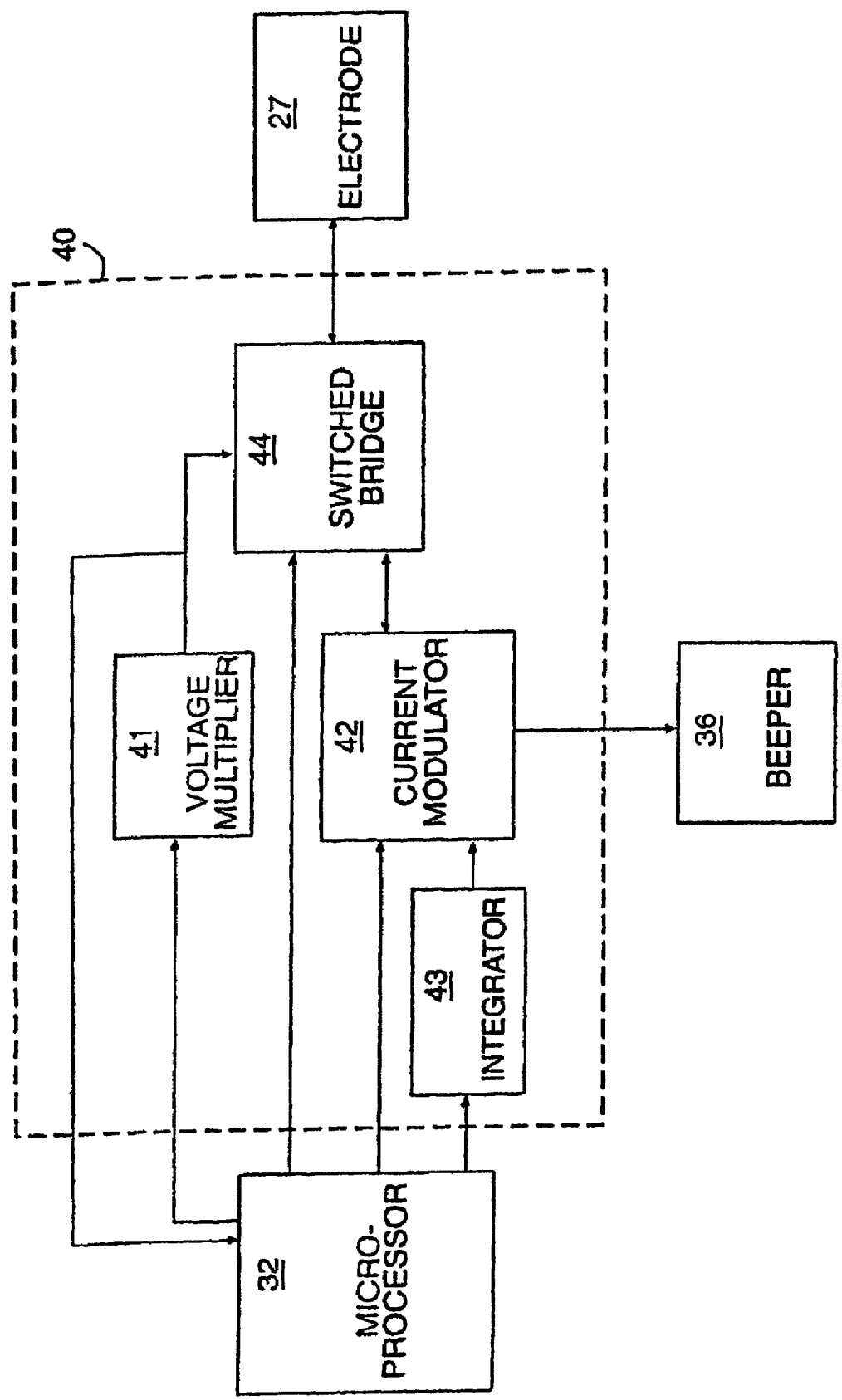
FIG. 3 is a schematic diagram of a waveform generator according to the embodiment of the present invention.

The waveform generator 40 is shown in more detail in FIG. 3. The waveform generator comprises a voltage multiplier 41, a current modulator 42, an integrator 43, and a switched bridge 44. The combined elements of the waveform generator 40 take power from the power supply 60 and generate a current waveform under control of the microprocessor 32.

The voltage multiplier supplies a voltage pumped signal to the switched bridge 44. In this embodiment, the voltage multiplier multiplies the battery voltage by 6. The voltage multiplier includes a voltage feedback loop with the microprocessor 32. The feedback voltage is fed to an ADC and software reduces the drive frequency to reduce the output voltage as required.

The switched bridge 44 supplies the generated current waveform to the electrode port 27. In this embodiment, the switched bridge 44 comprises four opto-isolators in a bridge configuration. In addition to the voltage pumped signal from the voltage multiplier 41, the switched bridge receives a polarity control signal from the microprocessor 32 and a current modulation signal from the current modulator 42. The integrator 42 processes the waveform signals received from the microprocessor 32 resulting in ramp, sine and square wave outputs as required. These outputs are sent to the current modulator 42. The current modulator 42 controls the output current level under direction of the microprocessor 32. The current range is controlled by a software-switchable sense resistor. The current modulator 42 receives signals from the integrator 43 and also receives current control signals from the microprocessor 32.

The microprocessor 32 supplies various signals to various portions of the waveform generator 40 so as to generate appropriate current waveforms. For example, the microprocessor 32 supplies a modulated square wave signal to the voltage multiplier 41, an output polarity setting to the switched bridge 44, a pulse width modulated synthesized waveform to the integrator 43 and a current level selection signal to the current modulator 42. The waveform parameters are stored in an EPROM and cannot be modified by the user. The microprocessor can be considered as being functionally part of the waveform generator. The waveform generator 40 supplies electrical signals to electrodes 50 via the electrode port 27.

In alternative embodiments the device may include two or more channels for simultaneously transmitting electrical signals to two or more electrode ports. A second channel may communicate with the first channel through an opto-isolator.

In further embodiments of the invention, the device 10 may include a display. In further embodiments, the microprocessor and the waveform generator may constitute one unit.

In yet further embodiments the device 10 may be programmed with two or more waveform treatment programs for generating a predetermined waveform or a predetermined sequence of waveforms. The device may further include further input switches to select between different waveform treatment programs.

Figure 4:
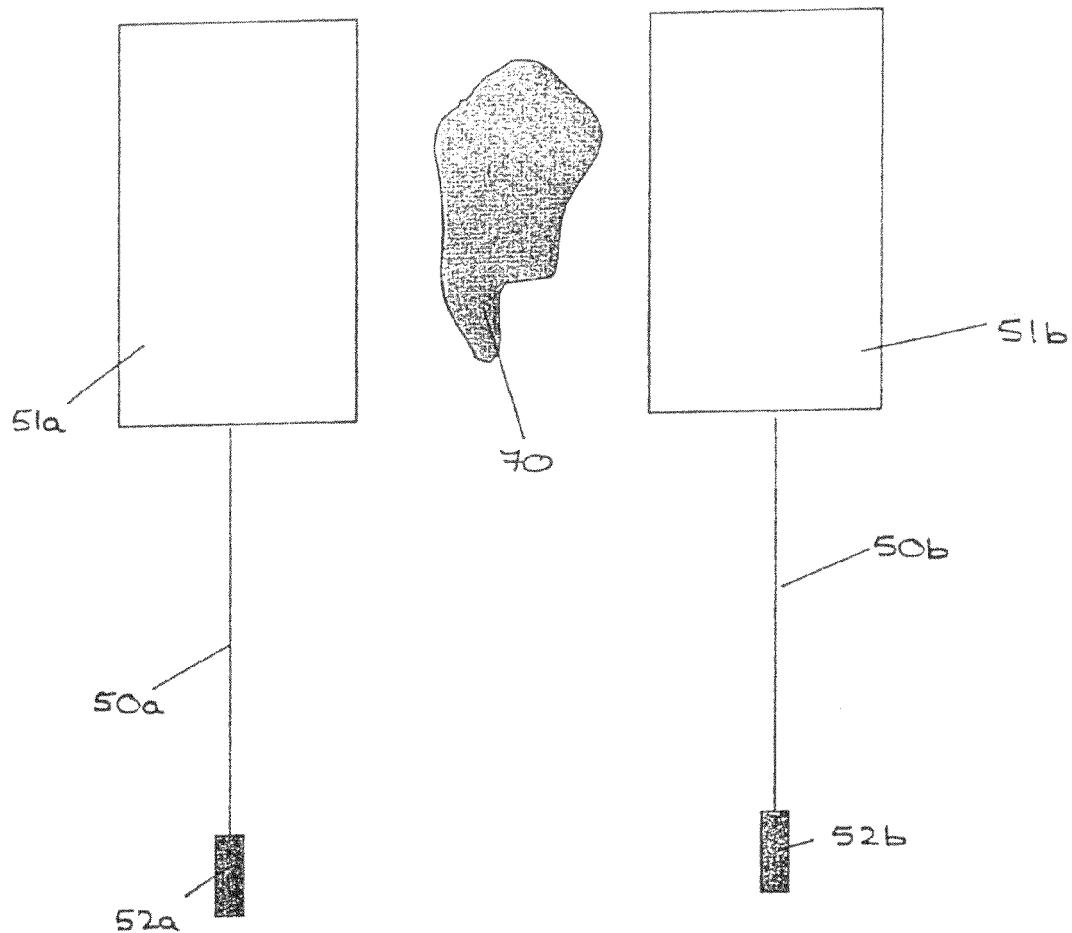
FIG. 4 is a schematic diagram of the area of treatment showing the disposition of electrode pads according to the embodiment of the present invention.

A method of treatment in accordance with an embodiment of the present invention will now be described with reference to FIGS. 4 to 6.

The method of the present invention includes steps of arranging electrodes around the area of body to be treated, covering the electrodes and the area of body to be treated with a compression bandage, providing a first electrotherapy waveform during a first treatment stage, providing a second electrotherapy waveform during a second treatment stage and providing a third electrotherapy waveform during a third treatment stage.

Figure 5:
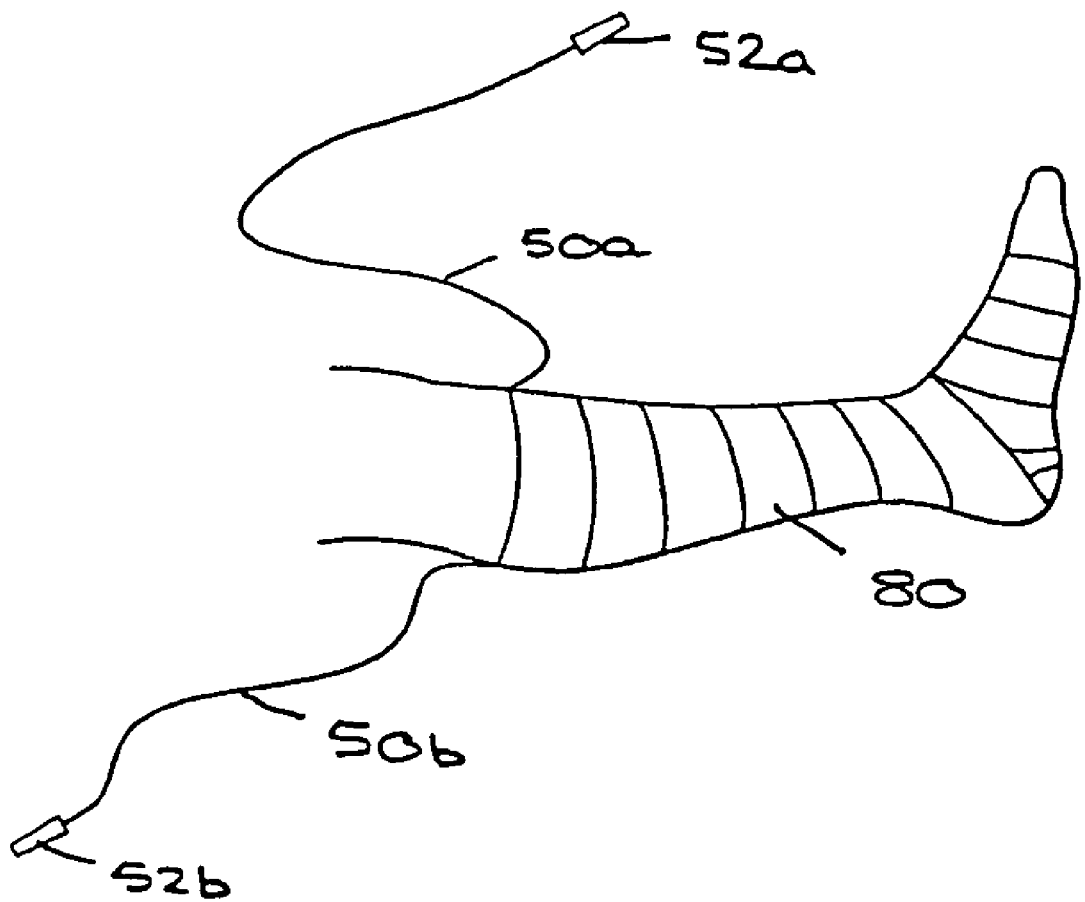
FIG. 5 is a simplified illustration of a method of treating a venous leg ulcer according to the embodiment of the invention.

The electrical waveforms are administered to an area of a body via a pair of electrode pads 51a and 51b which are placed on the surface of the skin on opposite sides of a wound 70 substantially parallel to the longitudinal axis of the wound as shown in FIG. 5. The electrode pads adhere to the skin of the patient and disperse current evenly across the surface. The electrode pads may be of any type known in electrotherapy and may be available in different sizes. The inner edge of the electrode pads are placed approximately 1 cm from the outer edges of the wound. The electrode pads extend approximately 1.5 cm from the outer edges of the wound in both directions substantially parallel to the longitudinal axis of the wound. The electrode pads are connected to a pair of electrode leads 50a and 50b which each have a connector 52a and 52b, respectively, at one end for connection to the device 10. Since the electrodes are placed outside the wound there is no need to remove and reapply any dressing on the wound and the wound is not irritated by contact with the electrode pads.

The method of the present invention according to this embodiment is particularly suited to the treatment of venous leg ulcers. The electrodes pads are placed around the wound on the leg and the leg is wrapped in a compression bandage 80 as shown in FIG. 6 Electrode leads 50a and 50b protrude from the compression bandaging 80 for connection to the electrotherapy device 10. The leads are between 5 m and 50 m in length. In this embodiment of the invention, a four layer compression bandaging system is used. The compression bandage applies pressure to the leg with greater pressure near the ankle and reduced pressure higher up. This forces the blood to keep circulating away from the lower leg and reduces blood pooling in the lower area. The improved blood flow aids in the healing of the wound. Since the electrode connectors protrude from the bandaging they are easily accessible for connection to the electrotherapy device and there is no need to wrap and unwrap the compression bandage. Since there is no need to unwrap the bandage each time treatment is administered this is practical for both the patient receiving treatment and the carer administering the treatment. Furthermore, the electrotherapy treatment works in combination with compression treatment providing benefits of the two treatments simultaneously to the patient.

Although FIG. 5 shows the electrode leads protruding from the top of the compression bandaging, in alternative embodiments the electrode leads may protrude from the side of the bandaging in the region of the wound so that the electrode leads do not have to be pressed along the length of the leg.

Figure 6A:
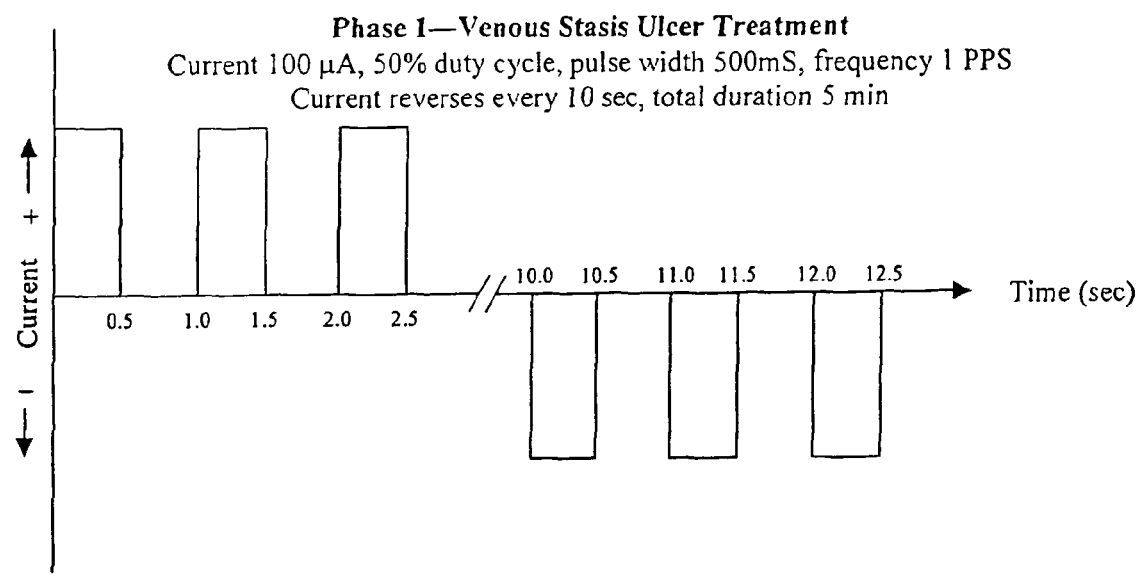
FIG. 6a is a graphical illustration of a first waveform generated by the embodiment of the present invention.

In a first stage of treatment the waveform illustrated in FIG. 6a is applied to the treatment area. The first treatment stage is particularly suited to reducing the resistance of the injured tissue. It has been proposed that injured tissue has a higher electrical resistance than healthy tissue such that the flow of natural electrical current through an injured section of the body is lower than the flow through normal surrounding tissue. The decreased electrical flow through the injured tissue decreases the cellular capacitance. Consequently, healing of the injured tissue is impaired. It has been further proposed that reducing the resistance of injured tissue and allowing the body's natural bio-electricity to enter the area would aid the healing process or reduce pain. To facilitate a change in tissue resistance the electrodes are provided with a waveform comprising a series of current pulses with an amplitude of 100 µA, having a frequency of 1 pulse per second (pps) and a pulse width of 500 ms. The pulses are substantially square and are characterised by a rapid rise to a current level, a hold at that current level, followed by a rapid return to near zero current. The polarity of the electrodes is reversed at periodic intervals of approximately 10 seconds. This stage of treatment lasts for 5 minutes.

Figure 6B:
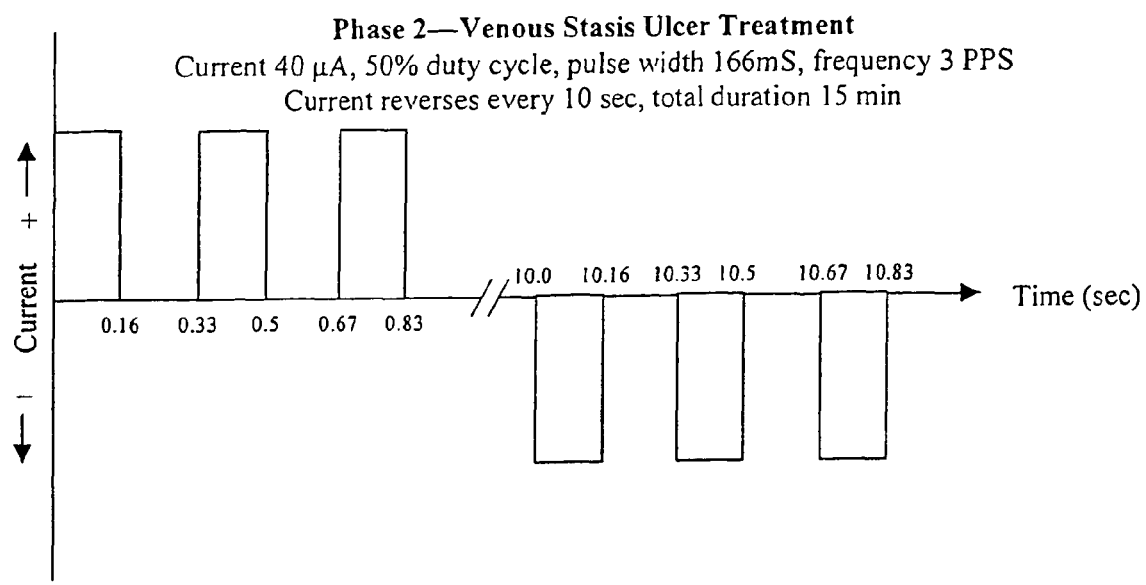
FIG. 6b is a graphical illustration of a second waveform generated by the embodiment of the present invention.

In a second stage of treatment the waveform illustrated in FIG. 6b is applied to the treatment area. The second stage of treatment is particularly suited to healing injured tissue by providing a current that mimics the body's natural current. To facilitate healing of the injured tissue the electrodes are provided with a waveform comprising a series of pulses with an amplitude of 40 µA, having a frequency of 3 pps and a pulse width of 166 ms. The polarity of the electrodes is reversed at periodic intervals of approximately 10 seconds. The second stage of treatment lasts for 15 minutes.

Figure 6C:
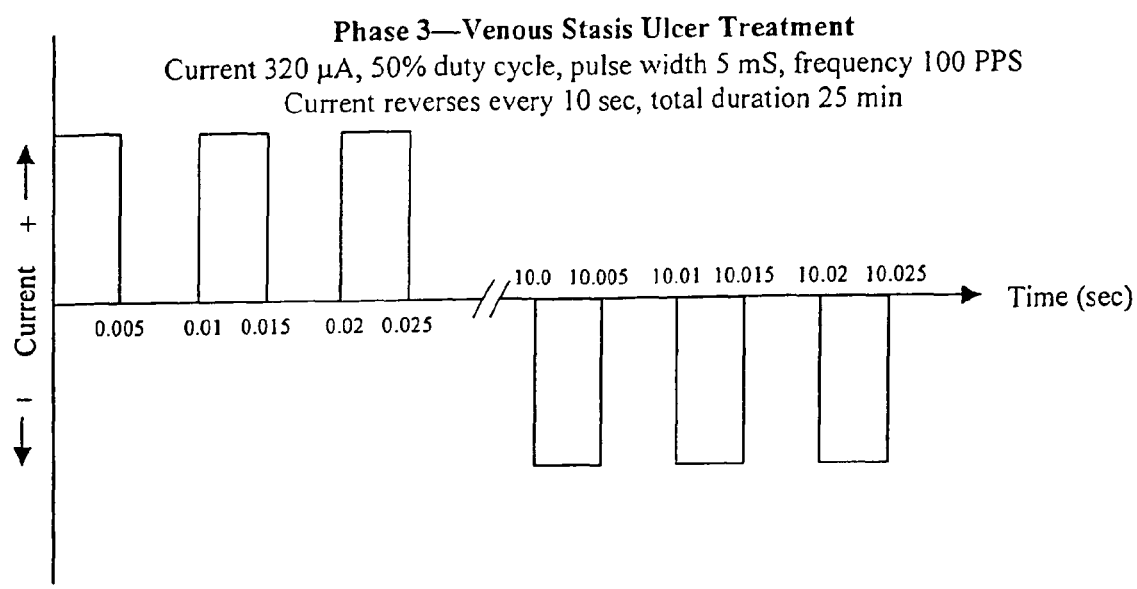
FIG. 6c is a graphical illustration of a third waveform generated by the embodiment of the present invention.

In a third stage of treatment the waveform illustrated in FIG. 6c is applied to the treatment area. The third stage of treatment is particularly suited to promoting blood vessel regeneration (angiogenesis). To facilitate blood vessel regeneration in injured tissue the electrodes are provided with a waveform comprising a series of pulses with an amplitude of 320 µA, having a frequency of 100 pps and a pulse width of 5 ms. The third treatment stage lasts for 25 minutes.

The three treatment stages are automatically executed sequentially. The second treatment stage follows the first treatment stage and the third treatment stage follows the second treatment stage. Since the three treatment stages are executed sequentially there is no need for further user interaction beyond starting the treatment program. The patient is free to relax and read a book or watch television while receiving treatment. The treatment can be administered by the patient himself in the comfort of his own home without the need to go to hospital. An advancement whereby the device is attached to the leg and requires zero interference by the patient as the device delivers currents automatically twice a day.

In a further embodiment of the invention, a plurality of pairs of electrodes may be placed around the wound. The inner edge of the electrode pads may be placed at different distances from the outer edges of the wound. Although in the embodiment described above the electrode pads extend beyond the area of the wound in alternative embodiments the electrodes may not extend beyond the area of the wound. In alternative embodiments the electrodes may be placed in the wound.

Although in the above described embodiment compression bandaging is used, as a compression covering, in alternative embodiments other types of compression coverings applying controlled pressure to veins to improve blood flow in the region of a wound, such as compression hosiery may be used.

In alternative embodiments of the invention, the waveform applied during the first treatment stage comprises a series of current pulses having an amplitude in a range of from 80 to 300 µA, having a frequency in a range from 0.5 to 1.5 pulses per second and a pulse width in a range from 333 to 1000 ms, the waveform applied during the second stage of treatment comprises a series of current pulses having an amplitude in a range of from 20 to 60 µA, having a frequency in a range from 2 to 4 pulses per second and a pulse width in a range from 125 to 250 ms, and the waveform applied during the third stage of treatment comprises a series of current pulses having an amplitude in a range of from 250 to 640 µA, having a frequency in a range of from 80 to 120 pulses per second and a pulse width in a range from 4 to 6 ms.

In alternative embodiments of the invention the polarity of the electrodes may be reversed at periodic intervals of approximately 5 to 15 seconds. In further embodiments the polarity of the electrodes may not be reversed.

While the treatment stages may last for longer or shorter periods, in another embodiment of the invention the first treatment stage lasts for a period of time ranging from 4 to 6 minutes, the second treatment stage lasts for a period of time ranging from 12 to 18 minutes, the second treatment stage lasts for a period of time ranging from 20 to 30 minutes. In a further embodiment of the invention, each treatment stage lasts for a period of time ranging from 5 to 30 minutes.

Although in the embodiment described hereinabove, the electrodes are placed either side of the wound, in one aspect the present invention is not so limited and electrodes could be placed on the wound e.g. in a wound dressing, when used with the waveforms described herein and compression coverings to provide improved wound healing.

Further, although the embodiment described hereinabove, a compression covering is used, in one aspect the present invention is not so limited. An improved wound treatment method can be achieved using electrodes either side of the wound and the waveforms described herein.

Although the present invention has been described with reference to specific embodiments, it will be apparent to a skilled person in the art that modifications lie within the spirit and scope of the present invention.

The invention claimed is:

1. A method of treating a wound on a limb, comprising:
   positioning a plurality of electrodes spaced apart in the region of the wound on the limb;
   reducing pooling of blood in the region of the wound by wrapping a compression bandage around the limb and over the electrodes and the region of the wound; and
   applying a sequence of current waveforms between the electrodes, wherein applying the sequence of current waveforms comprises:
   reducing the resistance of the wound by applying a first waveform comprising a series of current pulses having an amplitude in a range of from 80 to 300 µA, having a frequency in a range from 0.5 to 1.5 pulses per second and a pulse width in a range from 333 to 1000 ms;
   applying a second waveform comprising a series of current pulses having an amplitude in a range of from 20 to 60 µA, having a frequency in a range from 2 to 4 pulses per second and a pulse width in a range from 125 to 250 ms; and applying a third waveform comprising a series of current pulses having an amplitude in a range of from 250 to 640 µA, having a frequency in a range of from 80 to 120 pulses per second and a pulse width in a range from 4 to 6 ms.

2. A method of treating a wound according to claim 1, wherein the first waveform comprises a first part comprising said pulses of a first polarity and a second part comprising pulses of a second polarity.

3. A method of treating a wound according to claim 2, wherein during application of the first waveform the polarity of the electrodes is reversed approximately every 5 to 15 seconds.

4. A method of treating a wound according to claim 3, wherein during application of the first waveform the polarity of the electrodes is reversed at substantially every 10 seconds.

5. A method of treating a wound according to claim 2, wherein the first waveform is generated over a period of time ranging from 5 to 10 minutes.

6. A method of treating a wound according to claim 5, wherein the first waveform is generated over a time period of substantially 5 minutes.

7. A method of treating a wound according to claim 1, wherein the second waveform comprises a first part comprising said pulses of a first polarity and a second part comprising pulses of a second polarity.

8. A method of treating a wound according to claim 7, wherein during application of the second waveform the polarity of the electrodes is reversed approximately every 5 to 15 seconds.

9. A method of treating a wound according to claim 8, wherein during application of the second waveform the polarity of the electrodes is reversed at substantially every 10 seconds.

10. A method of treating a wound according to claim 7, wherein the second waveform is generated over a period of time ranging from 10 to 20 minutes.

11. A method of treating a wound according to claim 10, wherein the second waveform is generated over a period of time of substantially 15 minutes.

12. A method of treating a wound according to claim 1, wherein the third waveform comprises a first part comprising said pulses of a first polarity and a second part comprising pulses of a second polarity.

13. A method of treating a wound according to claim 12, wherein during application of the third waveform the polarity of the electrodes is reversed approximately every 5 to 15 seconds.

14. A method of treating a wound according to claim 13, wherein during application of the third waveform the polarity of the electrodes is reversed at substantially every 10 seconds.

15. A method of treating a wound according to claim 12, wherein the third waveform is generated over a period of time ranging from 15 to 30 minutes.

16. A method of treating a wound according to claim 15 wherein the third waveform is generated over a period of time of substantially 25 minutes.

17. A method of treating a wound according to claim 1, wherein the first waveform comprises a first part comprising said pulses of a first polarity and a second part comprising pulses of a second polarity, the second waveform comprises a first part comprising said pulses of a first polarity and a second part comprising pulses of a second polarity and the third waveform comprises a first part comprising said pulses of a first polarity and a second part comprising pulses of a second polarity.

18. A method of treating a wound according to claim 17, wherein during application of the first waveform the polarity of the electrodes is reversed approximately every 5 to 15 seconds, during application of the second waveform the polarity of the electrodes is reversed approximately every 5 to 15 seconds and during application of the third waveform the polarity of the electrodes is reversed approximately every 5 to 15 seconds.

19. A method of treating a wound according to claim 18, wherein during application of the first waveform the polarity of the electrodes is reversed at substantially every 10 seconds, during application of the second waveform the polarity of the electrodes is reversed at substantially every 10 seconds and during application of the third waveform the polarity of the electrodes is reversed at substantially every 10 seconds.

20. A method of treating a wound according to claim 17, wherein the first waveform is generated over a period of time ranging from 5 to 10 minutes, the second waveform is generated over a period of time ranging from 10 to 20 minutes, and the third waveform is generated over a period of time ranging from 15 to 30 minutes.

21. A method of treating a wound according to claim 20, wherein the first waveform is generated over a period of time of substantially 5 minutes, the second waveform is generated over a period of time of substantially 15 minutes, and the third waveform is generated over a period of time of substantially 25 minutes.

22. A method of treating a wound according to claim 20, wherein the electrodes are positioned in contact with skin around the wound.

23. A method of treating a wound according to claim 1, wherein
  the first waveform comprises a series of current pulses having an amplitude of substantially 100 µA, a frequency of substantially 1 pulse per second and a pulse width of substantially 500 ms;
  the second waveform comprises a series of current pulses having a amplitude of substantially 40 µA, a frequency of substantially 3 pulses per second and a pulse width of substantially 166 ms;
  the third waveform comprises a series of current pulses having an amplitude of substantially 320 µA, a frequency of substantially 100 pulses per second and a pulse width of substantially 5 ms.

24. A method of treating a wound according to claim 1, wherein the electrodes are positioned in contact with skin around the wound.

25. A method of treating a wound according to claim 24, wherein each electrode of a pair of electrodes is positioned on opposite sides of the wound to one another.

26. A method of treating a wound according to claim 24, wherein each electrode is placed approximately 1 cm from an edge of the wound.

27. A method of treating a wound according to claim 1, wherein the pulses are substantially rectangular.

28. A method of treating a wound according to claim 1, wherein the sequence of waveforms is repeated.

29. A method of treating a wound according to claim 1, wherein each end of each electrode extends beyond the outermost edges of the wound.

30. A method of treating a wound according to claim 29, wherein each end of each electrode extends beyond the outermost edges of the wound by approximately 1 to 1.5 cm.

31. A method of treating a wound according to claim 1, wherein said compression bandage is an elastic compression bandage.

32. A method of treating a wound on a limb comprising,
placing a plurality of electrodes in contact with skin in a region peripheral to the wound on the limb,
reducing pooling of blood in the region of the wound by wrapping a compression bandage around the limb and over the electrodes and the region of the wound; and
applying an electrical current to the plurality of electrodes;
wherein said applying an electrical current to the plurality of electrodes comprises applying a first current waveform comprising a series of current pulses having an amplitude in a range of from 80 to 300 µA, having a frequency in a range from 0.5 to 1.5 pulses per second and a pulse width in a range from 333 to 1000 ms.

33. A method of treating a wound according to claim 32, wherein said first current waveform reduces a resistance of injured tissue.

34. A method of treating a wound according to claim 32, wherein said applying an electrical current to the plurality of electrodes further comprises applying a second current waveform for healing injured tissue of the wound.

35. A method of treating a wound according to claim 34, wherein said second current waveform mimics natural currents of the body.

36. A method of treating a wound according to claim 34, wherein said applying an electrical current to the plurality of electrodes further comprises applying a third current waveform for promoting blood vessel regeneration.

* * * * *